US010466239B2

(12) United States Patent
Stoecker et al.

(10) Patent No.: US 10,466,239 B2
(45) Date of Patent: Nov. 5, 2019

(54) DIAGNOSIS OF A NEUROAUTOIMMUNE DISEASE

(71) Applicant: EUROIMMUN Medizinische Labordiagnostika AG, Lübeck (DE)

(72) Inventors: Winfried Stoecker, Groß Grönau (DE); Lars Komorowski, Ratzeburg (DE); Ramona Miske, Lübeck (DE); Yvonne Denno, Lübeck (DE); Madeleine Scharf, Lübeck (DE); Christian Probst, Ratzeburg (DE)

(73) Assignee: EUROIMMUN MEDIZINISHE LABORDIAGNOSTIKA AG, Lübeck (DE)

( * ) Notice: Subject to any disclaimer, the term of this patent is extended or adjusted under 35 U.S.C. 154(b) by 0 days.

(21) Appl. No.: 15/954,019

(22) Filed: Apr. 16, 2018

(65) Prior Publication Data

US 2018/0306787 A1 Oct. 25, 2018

(30) Foreign Application Priority Data

Apr. 20, 2017 (EP) .................................. 17000666

(51) Int. Cl.
| | | |
|---|---|---|
| *G01N 33/53* | (2006.01) | |
| *G01N 33/567* | (2006.01) | |
| *A61K 9/50* | (2006.01) | |
| *G01N 33/564* | (2006.01) | |
| *G01N 33/68* | (2006.01) | |
| *G01N 33/574* | (2006.01) | |

(52) U.S. Cl.
CPC ......... *G01N 33/564* (2013.01); *G01N 33/574* (2013.01); *G01N 33/57415* (2013.01); *G01N 33/57423* (2013.01); *G01N 33/6896* (2013.01); *G01N 2333/726* (2013.01)

(58) Field of Classification Search
None
See application file for complete search history.

(56) References Cited

U.S. PATENT DOCUMENTS

| | | | |
|---|---|---|---|
| 4,647,543 A | 3/1987 | Stöcker | |
| 7,087,716 B2 | 8/2006 | Wilm et al. | |
| 7,314,721 B2 | 1/2008 | Gure et al. | |
| 2008/0254482 A1 | 10/2008 | Mattoon et al. | |
| 2015/0355177 A1 | 12/2015 | Komorowski et al. | |
| 2016/0311876 A1 | 10/2016 | Miske et al. | |
| 2016/0355565 A1 | 12/2016 | Stoecker et al. | |

FOREIGN PATENT DOCUMENTS

| | | |
|---|---|---|
| EP | 2 423 226 A2 | 2/2012 |
| EP | 2 952 898 A1 | 12/2015 |
| EP | 3 018 478 A1 | 5/2016 |
| EP | 3 026 434 A1 | 6/2016 |
| EP | 3 086 120 A1 | 10/2016 |
| EP | 3 101 424 A1 | 12/2016 |
| ER | 01/85937 A2 | 11/2001 |
| WO | 2013/041540 A1 | 3/2013 |

OTHER PUBLICATIONS

Bansal et al., "R4 RGS Proteins: Regulation of G Protein Signaling and Beyond," *Pharmacol Ther* 116(3):473-495, 2007. (39 pages).
Extended European Search Report, dated Jul. 3, 2017, for European Application No. 17000666.2—1408, 7 pages.
Itoh et al., "Alternative splicing of RGS8 gene changes the binding property to the M1 muscarinic receptor to confer receptor type-specific Gq regulation," *Journal of Neurochemistry* 99:1505-1516, 2006.
Kveberg et al., "Expression of regulator of G protein signalling proteins in natural killer cells, and their modulation by Ly49A and Ly49D," *Immunology* 115:358-365, 2005.
Larminie et al., "Selective expression of regulators of G-protein signaling (RGS) in the human central nervous system," *Molecular Brain Research* 122:24-34, 2004.
Miske et al., "Autoantibodies against glutamate receptor δ2 after allogenic stem cell transplantation," *Neurology: Neuroimmunology & Neuroinflammation* 3:e255, 2016. (6 pages).
Miske et al., "Neurochondrin is a neuronal target antigen in autoimmune cerebellar degeneration," *Neurology: Neuroimmunology & Neuroinflammation* 4:e307, 2016. (9 pages).
Rodriguez-Lebron et al., "Altered Purkinje cell miRNA expression and SCA1 pathogenesis," *Neurobiology of Disease* 54:456-463, 2013.
Saitoh et al., "Distribution of regulator of G protein signaling 8 (RGS8) protein in the cerebellum," *The Cerebellum* 2:154-160, 2003.
Saitoh et al., "RGS8 expression in developing cerebellar Purkinje cells," *Biochemical and Biophysical Research Communications* 309:836-842, 2003.
Saitoh et al., "Regulator of G Protein Signaling 8 (RGS8) Requires Its $NH_2$ Terminus for Subcellular Localization and Acute Desensitization of G Protein-gated $K^+$ Channels," *The Journal of Biological Chemistry* 276(7):5052-5058, 2001. (8 pages).

(Continued)

*Primary Examiner* — Olga N Chernyshev
(74) *Attorney, Agent, or Firm* — Seed IP Law Group LLP

(57) ABSTRACT

The present invention relates to a method for diagnosing a disease comprising the step detecting in a sample comprising antibodies from a patient and also antibody binding to RGS8, a method for diagnosing a disease comprising the step detecting in a sample from a patient the level or activity of RGS8, a polypeptide comprising RGS8 or a variant thereof, a use of set polypeptide for the diagnosis of a disease, an antibody binding to RGS8, a use of the antibody for the diagnosis of the disease, a method for isolating an autoantibody binding to RGS8, a pharmaceutical composition or medical device comprising the polypeptide according to the present invention, a kit for the diagnosis of a disease comprising the polypeptide or the medical device according to the present invention and a use of the polypeptide, the antibody or the antibody for the manufacture of a kit or medical device.

5 Claims, 5 Drawing Sheets
(5 of 5 Drawing Sheet(s) Filed in Color)
Specification includes a Sequence Listing.

(56) References Cited

OTHER PUBLICATIONS

Saitoh et al., "RGS8 accelerates G-protein-mediated modulation of $K^+$ currents," *Nature* 390:525-529, 1997.

Scharf et al., "Neuronal $Na^+/K^+$ ATPase is an autoantibody target in paraneoplastic neurologic syndrome," *Neurology* 84:1-7, 2015. (8 pages).

Villasenor et al., "Rgs16 and Rgs8 in embryonic endocrine pancreas and mouse models of diabetes," *Disease Models & Mechanisms* 3:567-580, 2010.

DIAGNOSIS OF A NEUROAUTOIMMUNE DISEASE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310159_410_SEQUENCE_LISTING.txt. The text file is 12.1 KB, was created on Apr. 12, 2018, and is being submitted electronically via EFS-Web.

The present invention relates to a method for diagnosing a disease comprising the step detecting in a sample comprising antibodies from a patient and also antibody binding to RGS8, a method for diagnosing a disease comprising the step detecting in a sample from a patient the level or activity of RGS8, a polypeptide comprising RGS8 or a variant thereof, a use of set polypeptide for the diagnosis of a disease, an antibody binding to RGS8, a use of the antibody for the diagnosis of the disease, a method for isolating an autoantibody binding to RGS8, a pharmaceutical composition or medical device comprising the polypeptide according to the present invention, a kit for the diagnosis of a disease comprising the polypeptide or the medical device according to the present invention and a use of the polypeptide, the antibody or the antibody for the manufacture of a kit or medical device.

Developing diagnostic systems for neurological diseases is a continuing challenge in biomedical science, not in the least because many symptoms encountered may be accounted for by a huge variety of causes including genetically-inherited diseases, drug abuse, malnutrition, infection, injury, psychiatric illness, immunological defects and cancer.

Since a neurological disease is rarely associated with a unique characteristic pattern of clinical symptoms, it is often difficult to provide a reliable diagnosis solely based on the observation and examination of the patients affected or their medical history.

The importance of an early diagnosis cannot be overemphasized. Many neurological disorders, most prominently Alzheimer's and Parkinson's diseases as well as Multiple Sclerosis, cannot be cured, but drugs are available that may be used to slow down their progression. In addition, certain rare types of cancer are associated with neurological symptoms. The earlier the diagnosis, the better the chances to exploit the spectrum of available therapies to the full benefit of the patient.

This holds all the more true in the case of neurological diseases associated with autoantibodies. In some cases, the link between a specific detectable autoantibody and a condition is sufficiently strong to allow for an immediate diagnosis.

But even if it is not, the detection of autoantibodies may point the physician in charge to therapeutic means that may be used to ameliorate the patient's condition. There is a variety of widely used immunosuppressants that may be used regardless of the nature of the autoantibody's target. Alternatively, apheresis may be used to remove autoantibodies from the patient's blood. In many cases, patients went on to lead a normal life following early diagnosis and treatment of a neurological autoimmune disease.

Diagnostic assays based on the detection of autoantibodies may also corroborate the diagnosis of diseases other than those associated with autoantibodies. If it turns out that a blood sample is devoid of specific autoantibodies, this is likely to help the physician in charge exclude a range of possibilities and thus narrow down the spectrum of plausible conditions.

Examples of neurological conditions coinciding with the emergence of autoantibodies include Neuromyelitis optica, a disease characterized by loss of vision and spinal cord function, and anti-NMDA receptor encephalitis, which is associated with autonomic dysfunction, hypoventilation, cerebellar ataxia, hemiparesis, loss of consciousness, or catatonia. Whilst the involvement of autoantibodies and the nature of these conditions as such was previously poorly understood, many of this disease can now be diagnosed and treated efficiently owing to the availability of assays based on the detection of autoantibodies.

Therefore, it is paramount that new approaches be developed to distinguish neurological conditions associated with autoantibodies from those that are not.

US 2008/0254482A1 discloses biomarkers associated with Rheumatoid Arthritis (RA), Systemic Lupus Erythematodes (SLE) and Anti-Neutrophil Cytoplasmic Antibody (ANCA). In Table 10 RGS8 is listed as one of >100 proteins bound to an antibody from one SLE patient. There is no corroborating experimental data or instruction regarding the existence, let alone diagnostical usefulness of this antibody.

U.S. Pat. No. 7,087,716B2 discloses an isolated polypeptide comprising RGS8, but does not comprise any experimental data. The existence, let alone diagnostic usefulness of an autoantibody to RGS8 is not disclosed.

The problem underlying the present invention is to provide novel reagents, devices and methods that may be used to support the diagnosis and treatment of a neurological disease, in particular of a neurological disease, preferably an autoimmune disease of the nervous system, more preferably selected from the group comprising cerebellar syndrome, cerebellitis and PNS (paraneoplastic neurological syndrome), preferably PNS.

Another problem underlying the present invention is to provide novel reagents, devices and methods that may be used to distinguish autoimmune diseases, in particular neurological autoimmune diseases, from diseases other than autoimmune diseases, not in the least to determine the most promising treatment regimen, more specifically whether or not an immunosuppressive treatment is adequate.

The problem underlying the present invention is solved by the subject-matter of the attached independent and dependent claims.

In a $1^{st}$ aspect, the problem underlying the present invention is solved by a method for diagnosing a disease comprising the step detecting in a sample comprising antibodies from a patient an autoantibody binding RGS8.

In a $2^{nd}$ aspect, the problem underlying the present invention is solved by a method for diagnosing a disease comprising the step detecting in a sample or tissue expressing RGS8 from a patient the level or activity of RGS8, preferably exposed to antibodies.

In a $3^{rd}$ aspect, the problem underlying the present invention is solved by a polypeptide comprising RGS8 or a variant thereof, which is preferably immobilized, more preferably on a solid carrier.

In a $4^{th}$ aspect, the problem underlying the present invention is solved by a use of a polypeptide according to the present invention for the diagnosis of a disease, preferably comprising the step detecting in a sample an autoantibody binding to RGS8.

In a preferred embodiment, the polypeptide according to the present invention is for use in a treatment of a disease.

In a 5th aspect, the problem underlying the present invention is solved by an antibody, preferably an isolated autoantibody, more preferably an isolated autoantibody, binding to RGS8, wherein the autoantibody is preferably in complex with the polypeptide according to the present invention.

In a 6th aspect, the problem underlying the present invention is solved by a use of an antibody, preferably autoantibody, according the present invention for the diagnosis of a disease.

In a 7th aspect, the problem underlying the present invention is solved by method for isolating an autoantibody binding to RGS8 comprising the steps
a) contacting a sample comprising the autoantibody with a polypeptide according to the present invention under conditions compatible with formation of a complex, wherein said autoantibody binds to said polypeptide,
b) isolating the complex formed in step a),
c) dissociating the complex isolated in step b) and
d) separating the autoantibody from the polypeptide.

In a 7th embodiment the problem underlining the present invention is solved by a pharmaceutical composition or medical device, preferably diagnostic device, comprising the polypeptide according to the present invention.

In an 8th aspect, the problem underlying the present invention is solved by a kit for the diagnosis of a disease, which kit comprises the polypeptide according the present invention of the medical device according the present invention,
wherein preferably the kit comprises in addition a means for detecting a complex comprising the polypeptide according to present invention and an antibody binding to RGS8.

In a preferred embodiment, the patient has or the disease is associated with one or more, preferably two or more symptoms selected from the group comprising dysarthria, dysphagia, nystagmus, oscillopsia, vertigo, nausea, ataxia, dizziness, seizures, epilepsy and tremor.

In an 9th aspect, the problem underlying the present invention is solved by a use of a polypeptide according the present invention, the antibody according the present invention or the medical device according to the present invention for the manufacture of a kit, medical device, preferably diagnostic device, for the diagnosis of a disease.

In a preferred embodiment, the disease is a neurological disease, preferably an autoimmune disease of the nervous system, more preferably selected from the group comprising cerebellar syndrome, cerebellitis and PNS, preferably PNS.

In a preferred embodiment, the disease is cancer, preferably a cancer from the group comprising Hodgkin lymphoma, non-Hodgkin lymphoma, small cell lung carcinoma and breast cancer, preferably a lymphoma or small cell lung carcinoma, more preferably small cell lung carcinoma.

In a preferred embodiment, the sample is a bodily fluid comprising antibodies, preferably selected from the group comprising whole blood, serum, cerebrospinal fluid and saliva, or the sample is a tumor biopsy.

The present invention is based on the inventors' surprising finding that a neurological autoimmune disease associated with cancer exists that is associated with an autoantibody to RGS8.

Furthermore, the present invention is based on the inventors' surprising finding that autoantibodies to RGS8 exist and may be detected in samples from a number of patients suffering from neurological symptoms and/or cancer, but not in samples obtained from healthy subjects.

Furthermore, the present invention is based on the inventors' surprising finding that the novel neurological disease and/or cancer may be diagnosed by the way of detection of autoantibodies to RGS8.

Furthermore, the present invention is based on the inventors' surprising finding that cancer may be diagnosed by way of detecting the level or activity of RGS8 or tissue expressing RGS8, preferably exposed to antibodies.

Without wishing to be bound to any theory, the presence of such autoantibodies suggests that activity and function of RGS8 and/or downstream effectors is impaired in patients having such autoantibodies to the effect that neurological symptoms or cancer occur.

Regulator of G-protein signaling 8 (RGS8) is an intracellular peripheral membrane protein. It regulates heterotrimeric G-proteins by stimulating the GTPase activity of G-protein alpha-i/o and alpha-q subunits, driving them into their inactive GDP-bound form. Thereby, RGS8 influence G protein-coupled receptor signaling, including signaling via muscarinic acetylcholine receptor (mAChR). However, overexpression of RGS8 led not only to increased "off" kinetics of G-protein-coupled channels, but also to faster activation kinetics, suggesting that RGS8 is not just a simple negative regulator (Saitoh O., Kubo Y., Miyatani Y, Asano T, Nakata H., 1997, RGS8 accelerates G-protein-mediated modulation of K+ currents, Nature, 390(6659):525-9; Itoh M, Nagatomo K, Kubo Y, Saitoh O., 2006, Alternative splicing of RGS8 gene changes the binding property to the M1 muscarinic receptor to confer receptor type-specific Gq regulation., J Neurochem. 99(6): 1505-16).

RGS8 is predominantly expressed in the brain, especially in the cell body and dendrites of cerebellar Purkinje cells. (Larminie C, Murdock P, Walhin J P, Duckworth M, Blumer K J, Scheideler M A, Gamier M., 2004, Selective expression of regulators of G-protein signaling (RGS) in the human central nervous system. Brain Res Mol Brain Res. 122(1): 24-34). In non-neural cells transfected with RGS8 cDNA, the protein localizes in nuclei. After co-expression of constitutively active Galphao, RGS8 protein translocated to the plasma membrane (Saitoh O, Masuho I, Itoh M, Abe H, Komori K, Odagiri M., 2003, Distribution of regulator of G protein signaling 8 (RGS8) protein in the cerebellum. Cerebellum. 2(2):154-160). Furthermore, RGS8 was shown to be expressed in rat natural killer (NK) cells as well as pancreatic progenitor and endocrine cells (Kveberg L, Ryan J C, Rolstad B, Inngjerdingen M., 2005, Expression of regulator of G protein signalling proteins in natural killer cells, and their modulation by Ly49A and Ly49D, Immunology; 115(3):358-65; Villasenor A, Wang Z V, Rivera L B, Ocal O, Asterholm I W, Scherer P E, Brekken R A, Cleaver O, Wilkie T M, 2010, Rgs16 and Rgs8 in embryonic endocrine pancreas and mouse models of diabetes, Dis Model Mech., 3(9-10):567-80.)

RGS8 is a 21-kDa protein containing 180 amino acids. Like all of the 22 identified RGS proteins, RGS8 contains a RGS domain, which mediates G-alpha subunits binding. It belongs to the B/R4 subfamily of RGS proteins. Members of this subfamily are characterized by an N-terminal PDZ domain, followed by a proline, glutamine, serine, threonine-rich (PEST) region, acidic amino acids and a C-terminal RGS domain, assigned to amino acid 56-171 in RGS8 (reviewed in Geetanjali B., Kirk M D., Zhihui X., 2007, R4 RGS Proteins: Regulation of G Protein Signaling and Beyond, Pharmacol Ther.; 116(3): 473-495)

The present invention relates to a polypeptide comprising a mammalian, preferably human RGS8 or variants thereof, preferably immunogenic variants reactive to autoantibodies binding to RGS8 or variants thereof. Examples of mammalian RGS8 include those from human, monkey, mouse, rat, rabbit, guinea pig or pig. In a most preferred embodiment, RGS8 is the polypeptide encoded by the data base code P57771-1 or P57771-2, preferably P57771-1. The data base codes of the corresponding cDNA are BC069677 (NCBI) and SEQ ID NO: 18, respectively. Throughout this application, any data base codes cited refers to the Uniprot data base, more specifically the version on the filing date of this application or its earliest priority application.

The teachings of the present invention may not only be carried out using polypeptides, in particular a polypeptide comprising the native sequence of RGS8, or nucleic acids having the exact sequences referred to in this application explicitly, for example by function, name, sequence or accession number, or implicitly, but also using variants of such polypeptides or nucleic acids.

In a preferred embodiment, the term "variant", as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150 or 200 successive amino acids of the original sequence or a variant thereof. The total length of the variant may be at least 6, 7, 8, 9, 10, 11, 12, 20, 25, 30, 40, 50, 60, 70, 80, 90, 100 or more amino acids.

In another preferred embodiment, the term "variant" relates not only to at least one fragment, but also to a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3$^{rd}$ edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings.

In a preferred embodiment, the variant is a linear, non-folded fragment.

In a preferred embodiment, the polypeptide and variants thereof may, in addition, comprise chemical modifications, for example isotopic labels or covalent modifications such as glycosylation, phosphorylation, acetylation, decarboxylation, citrullination, methylation, hydroxylation and the like. The person skilled in the art is familiar with methods to modify polypeptides. Any modification is designed such that it does not abolish the biological activity of the variant.

Moreover, variants may also be generated by fusion with other known polypeptides or variants thereof and comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In a preferred embodiment, the term "variant" of a nucleic acid comprises nucleic acids the complementary strand of which hybridizes, preferably under stringent conditions, to the reference or wild type nucleic acid. Stringency of hybridization reactions is readily determinable by one of ordinary skilled in the art, and in general is an empirical calculation dependent on probe length, washing temperature and salt concentration. In general longer probes require higher temperatures for proper annealing, while shorter probes less so. Hybridization generally depends on the ability of denatured DNA to reanneal to complementary strands present in an environment below their melting temperature: The higher the degree of desired homology between the probe and hybridizable sequence, the higher the relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the probe is 70% or more identical to the target sequence. Probes having a lower degree of identity with respect to the target sequence may hybridize, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence and variants thereof as the reference nucleic acid sequence, in line with the degeneracy of the genetic code.

The variant of the polypeptide has biological activity. In a preferred embodiment, such biological activity is the ability to bind to the autoantibody binding to RGS8 found in a patient suffering from an autoimmune disease associated with autoantibodies to RGS8, preferably associated with a neurological disease such as cerebellar syndrome, cerebellitis and PNS or a cancer, preferably from the group comprising Hodgkin lymphoma, non-Hodgkin lymphoma, small cell lung and breast cancer, preferably a lymphoma or small cell lung carcinoma, more preferably small cell lung carcinoma, preferably PNS associated with an autoantibody to RGS8.

The inventive polypeptide, which comprises RGS8 or a variant thereof, or the inventive autoantibody, when used to carry out the teachings of the present invention, may be provided in any form and at any degree of purification, from liquid samples, tissues or cells comprising said polypeptide in an endogenous form, more preferably cells overexpressing the polypeptide, crude or enriched lysates of such cells, to purified and/or isolated polypeptide which is optionally essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification," "Antibody Purification," "Purifying Challenging Proteins" (2009/2010), published by GE Healthcare Life Sciences, and in Burgess, R. R., Deutscher, M. P. (2009), Guide to Protein Purification). In a preferred embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection.

If the inventive polypeptide is provided in the form of tissue, it is preferred that the tissue is mammalian tissue, for example human, rat, primate, donkey, mouse, goat, horse, sheep, pig or cow, more preferably brain tissue, most preferably cerebellum. If a cell lysate is used, it is preferred that the cell lysate comprises the membranes associated with the surface of the cell. If said polypeptide is provided in the form of a recombinant cell, it is preferred that the recombinant cell is a eukaryotic cell such as a yeast cell, more preferably a cell from a multicellular eukaryote such as a plant, mammal, frog or insect, most preferably from a mammal, for example rat, human, primate, donkey, mouse, goat, horse, sheep, pig or cow.

The polypeptide used to carry out the inventive teachings, including any variants, is preferably designed such that it comprises at least one epitope recognized by and/or binds specifically to autoantibodies binding to RGS8. Any epitope is more preferably an epitope recognized by such an autoantibody only, by contrast to antibodies other than an autoantibody to RGS8. In one embodiment, such polypeptide comprises a stretch of 6, 7, 8, 9, 10, 11, 12, 20, 25, 30, 40, 50, 60, 70, 80, 90, 100 or more, preferably at least 9 but no more than 16, consecutive amino acids from RGS8. The person skilled in the art is familiar with guidelines used to design peptides having sufficient immunogenicity, for example those described in Jackson, D. C., Fitzmaurice, C. J., Brown, L. E., Zeng, W. (1999), Preparation and properties of totally synthetic immunogens, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173. Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) is has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71. SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15 represent major epitopes of RGS8.

The inventive polypeptide, which comprises RGS8 or a variant thereof, when used according to the present invention, may be provided in any kind of conformation. For example, the polypeptide may be an essentially unfolded, a partially or a fully folded polypeptide. In a preferred embodiment, the polypeptide is folded in the sense that the epitopes essential for the binding to the inventive autoantibody, or the protein or variant thereof in its entirety, adopt the fold adopted by the native protein in its natural environment. The person skilled in the art is familiar with methods suitable to determine whether or not a polypeptide is folded and if it is, which structure it has, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably CD spectroscopy is used.

The inventive polypeptide may be a fusion protein which comprises amino acid sequences other than those taken from RGS8, in particular a C-terminal or N-terminal tag, preferably a C-terminal tag, which is, in a preferred embodiment, as used herein, an additional sequence motif or polypeptide having a function that has some biological or physical function and may, for example, be used to purify, immobilize, precipitate or identify the inventive polypeptide. In a more preferred embodiment, the tag is a sequence or domain capable of binding specifically to a ligand, for example a tag selected from the group comprising His tags, thioredoxin, maltose binding protein, glutathione-S-transferase, a fluorescence tag, for example from the group comprising green fluorescent protein.

The inventive polypeptide may be an immobilized polypeptide. In a preferred embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Various suitable carriers, for example paper, polystyrene, metal, silicon or glass surfaces, microfluidic channels, membranes, beads such as magnetic beads, column chromatography media, biochips, polyacrylamide gels and the like have been described in the literature, for example in Kim, D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, and A. E. (2013), Protein immobilization techniques for microfluidic assays, Biomicrofluidics 7(4), 041501. In addition, various reagents and kits for immobilization reactions are commercially available, for example from Pierce Biotechnology.

It is essential that the sample used for the diagnosis in line with the detection of autoantibodies according to the present invention comprises antibodies, also referred to as immunoglobulins. Typically the sample of a bodily fluid comprises a representative set of the entirety of the subject's immunoglobulins. However, the sample, once provided, may be subjected to further processing which may include fractionation, centrifugation, enriching or isolating the entirety of immunoglobulins or any immunoglobulin class of the subject, which may affect the relative distribution of immunoglobulins of the various classes.

The reagents, devices, methods and uses described throughout this application may be used for the diagnosis of a disease. In a preferred embodiment, the disease is a neurological disease. In a more preferred embodiment, the term "neurological disease", as used herein, refers to any disease associated with a defect of the nervous system, in another preferred embodiment, the term "PNS", abbreviation of paraneoplastic neurological syndrome, as used herein, refers to a systemic disorder indirectly caused by the presence of a tumor, for example, as a result of the production release of substances such as hormones or cytokines not normally produced by the cell of origin of the tumor or are produced at increased concentration or the production and release of biologically active cells.

In another preferred embodiment, the disease is a cancer, preferably selected from the group comprising lymphoma, preferably B-cell lymphoma of the stomach, or non-Hodgkin's lymphoma, small cell lung carcinoma and occult tumor breast cancer, cancer of the ovaries such as teratoma.

In a preferred embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from a certain disease or disorder in the past, at the time of the diagnosis or in the future, to find out how the disease is progressing or is likely to progress in the future or to evaluate the responsiveness of a patient with regard to a certain treatment, for example the administration of immunosuppressive drugs. In other words, the term "diagnosis" comprises not only diagnosing, but also prognosticating and/or monitoring the course of a disease or disorder.

In many cases the mere detection, in other words determining whether or not detectable levels of the antibody are present in the sample, is sufficient for the diagnosis. If the autoantibody can be detected, this will be information instrumental for the clinician's diagnosis and indicates an increased likelihood that the patient suffers from a disease. In a preferred embodiment, the relative concentration of the antibody in the serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 0.1, preferably 0.2, 0.5, 1, 2, 5, 10, 20, 25, 50, 100, 200, 500, 1000, 10000 or 100000 times higher than the concentration found in the average healthy subject.

The person skilled in the art will appreciate that a clinician does usually not conclude whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other non-invasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. In a preferred embodiment, the meaning of any symptoms or diseases referred to throughout this application is in line with the person skilled in the art's understanding as of May 29, 2015 as evidenced by text books and scientific publications.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i. e. a systematic diagnostic procedure considering the likelihood of a range of possible conditions on the basis of a range of diagnostic parameters. Consequently, the inventive method, polypeptide or use, optionally for determining whether a patient suffers from the a disease, may comprise obtaining a sample from a patient, preferably a human patient, determining whether an autoantibody binding to RGS8 is present in said sample, wherein said determining is performed by contacting the sample with the inventive polypeptide and detecting whether binding occurs between said polypeptide and said autoantibody, preferably using a labeled secondary antibody, wherein said autoantibody binds to said polypeptide if present in the sample, and diagnosing the patient as suffering or being more likely to suffer from said neurological disorder or cancer if the autoantibody was determined to be present in the sample. In a preferred embodiment, the inventive method may contemplate the steps detecting an antibody to a) SOX1 and b) RGS8, preferably in that order.

The term "diagnosis" may also refer to a method or agent used to distinguish between two or more conditions associated with similar or identical symptoms.

The term "diagnosis" may also refer to a method or agent used to choose the most promising treatment regime for a patient. In other words, the method or agent may relate to selecting a treatment regimen for a subject. For example, the detection of autoantibodies may indicate that an immunosuppressive therapy is to be selected, which may include administrating to the patient one or more immunosuppressive drugs.

The present invention relates to a complex comprising an antibody, preferably autoantibody, binding to the inventive polypeptide. Such a complex may be used or detected as part of a method for diagnosing a disease. A liquid sample comprising antibodies from a subject may be used to practice the method if autoantibodies to RGS8 are to be detected. Such a liquid sample may be any bodily fluid comprising a representative set of antibodies from the subject, preferably a sample comprising antibodies of the IgG immunoglobulin class from the subject. For example, a sample may be cerebrospinal fluid (CSF), blood or blood serum, lymph, insterstitial fluid and is preferably serum or CSF, more preferably serum.

In a preferred embodiment, the level of RGS8 in a sample such as a serum sample or in tissue expressing RGS8 such as a tumor biopsy is detected. The term "level", as used herein, may refer to the concentration, expression or activity of RGS8. The concentration may be used by ELISA, semi-quantitative Westernblotting, or quantitative immunohistostaining, preferably ELISA. The expression may be detected by quantifying the concentration of mRNA, for example by RT PCR. The activity of RGS8 may be quantified by the G protein binding assay described in Saitoh et al. (2000) Regulator of G Protein Signaling (RGS8) Requires its NH2 terminus for subcellular localization and acute desensitization of G-Protein gated K+ Channels, J. Biol. Chem. 276, 5052-5058. In another preferred embodiment, the RGS8 concentration or activity or presence of RGS8-expressing cells such an circulating tumor cells is detected in blood.

The step contacting a liquid sample comprising antibodies with the inventive polypeptide may be carried out by incubating an immobilized form of said polypeptide in the presence of the sample comprising antibodies under conditions that are compatible with the formation of the complex comprising said polypeptide and an antibody, preferably an autoantibody, binding to the inventive polypeptide. The liquid sample, then depleted of antibodies binding to the inventive polypeptide may be removed subsequently, followed by one or more washing steps. Finally the complex comprising the antibody and the polypeptide may be detected. In a preferred embodiment, the term "conditions compatible with the formation of the complex" are conditions that allow for the specific antigen-antibody interactions to build up the complex comprising the polypeptide an the antibody. In a preferred embodiment such conditions may comprise incubating the polypeptide in sample diluted 1:100 in PBS buffer for 30 minutes at 25° C. In a preferred embodiment, the term "autoantibody", as used herein, refers to an antibody binding specifically to an endogenous molecule of the animal, preferably mammal, which produces said autoantibody, wherein the level of such antibody is more preferably elevated compared the average of any other antibodies binding specifically to such an endogenous molecule. In a most preferred embodiment, the autoantibody is an autoantibody binding to RGS8.

The method according to the present invention is preferably an in vitro method.

In a preferred embodiment, the detection of the complex for the prognosis, diagnosis, methods or test kit according to the present invention comprises the use of a method selected from the group comprising immunodiffusion techniques, immunoelectrophoretic techniques, light scattering immunoassays, light scattering immunoassays, agglutination techniques, labeled immunoassays such as those from the group comprising radiolabeled immunoassay, enzyme immunoassays, chemiluminescence immunoassays, and immunofluorescence techniques. The person skilled in the art is familiar with these methods, which are also described in the state of the art, for example in Zane, H. D. (2001), Immunology—Theoretical & Practical Concepts in Laboratory Medicine, W. B. Saunders Company, in particular in Chapter 14.

Alternatively, a sample comprising tissue comprising the inventive polypeptide rather than a liquid sample may be used. The tissue sample is preferably from a tissue expressing endogenous RGS8. Such a sample, which may be in the form of a tissue section fixed on a carrier, for example a glass slide for microscopic analysis, may then be contacted with the inventive antibody, preferably autoantibody, binding to the inventive polypeptide. The antibody is preferably labeled to allow for distinction from endogenous antibodies binding to the inventive polypeptide, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and the inventive polypeptide may be correlated with reference data. For example, detection of said complex indicates that the patient who provided the sample analyzed has suffered, is suffering or is likely to suffer in the future from a disease. If a patient has been previously diagnosed and the method for obtaining diagnostically relevant information is run again, the amount of complex detected in both runs may be correlated to find out about the progression of the disease and/or the success of a treatment. For example, if the amount of complex is found to increase, this suggests that the disorder is progressing, likely to manifest in the future and/or that any treatment attempted is unsuccessful.

In a preferred embodiment, a microtiterplate, membrane ELISA, dot blot, or line blot is used to carry out the diagnostic method according to the invention. The person skilled in the art is familiar with the experimental setup, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540).

In another preferred embodiment, the prognosis, diagnosis, methods or test kit in line with the inventive teachings contemplate the use of indirect immunofluorescence. The person skilled in the art is familiar with such techniques and the preparation of suitable samples, which are described in the state of the art (U.S. Pat. No. 4,647,543; Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007). Suitable reagents, devices and software packages are commercially available, for example from EUROIMMUN, Lübeck, Germany.

A sample subjected to a test determining only whether an autoantibody binding to RGS8 is present, but it is preferred that diagnostic methods, tests, devices and the like contemplate determining the presence of autoantibodies to one or more antigens relating to neurological autoimmune disease or variants thereof, preferably selected from the group comprising Hu, Yo, Ri, CV2, PNMA1, PNMA2, DNER/Tr, ARHGAP26, ITPR1, ATP1A3, NBC1, Neurochrondrin, CARPVIII, Zic4, Sox1, Ma, MAG, MP0, MBP, GAD65, amphiphysin, recoverin, GABA A receptor, GABA B receptor, glycine receptor, gephyrin, IgLON5, DPPX, aquaporin-4, MOG, NMDA receptor, AMPA receptors, GRM1, GRM5, LGI1, VGCC and mGluR1 and CASPR2, which antigens are preferably immobilized, for example on a medical device such as a line blot. In a more preferred embodiment, an autoantibody to RGS8 and an autoantibody to SOX1 (U.S. Pat. No. 7,314,721) is detected. The diagnostically relevant markers Neurochrondrin (EP15001186), ITPR1 (EP14003703.7), NBC1 (EP14003958.7), ATP1A3, also referred to as alpha 3 subunit of human neuronal Na(+)/K(+) ATPase (EP14171561.5) and Flotillin1/2 (EP3101424) have been described in the state of the art.

According to the teachings of the present invention, an antibody, preferably an autoantibody binding to the inventive polypeptide is used for the diagnosis of a disease is provided. The person skilled in the art is familiar with methods for purifying antibodies, for example those described in Hermanson, G. T., Mallia, A. K., and Smith, P. K. (1992), Immobilized Affinity Ligand Techniques, San Diego: Academic Press. Briefly, an antigen binding specifically to the antibody of interest, which antigen is the inventive polypeptide, is immobilized and used to purify, via affinity chromatography, the antibody of interest from an adequate source. A liquid sample comprising antibodies from a patient suffering from the neurological disorder identified by the inventors may be used as the source.

According to the invention, an antibody, for example an autoantibody, is provided that is capable of binding specifically to the inventive polypeptide. In a preferred embodiment, the term "antibody", as used herein, refers to any immunoglobulin-based binding moieties, more preferably one comprising at least one immunoglobulin heavy chain and one immunoglobulin light chain, including, but not limited to monoclonal and polyclonal antibodies as well as variants of an antibody, in particular fragments, which binding moieties are capable of binding to the respective antigen, more preferably binding specifically to it. In a preferred embodiment, the term "binding specifically", as used herein, means that the binding is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7. The antibody may be part of an autoantibody preparation which is heterogeneous or may be a homogenous autoantibody, wherein a heterogeneous preparation comprises a plurality of different autoantibody species as obtainable by preparation from the sera of human donors, for example by affinity chromatography using the immobilized antigen to purify any autoantibody capable of binding to said antigen. The antibody may be glycosylated or non-glycosylated. The person skilled in the art is familiar with methods that may be used for the identification, production and purification of antibodies and variants thereof, for examples those described in EP 2 423 226 A2 and references therein. The antibody may be used as a diagnostic agent, by itself, or in combination, for example in complex with the inventive polypeptide.

The present invention provides a method for isolating an antibody, preferably an autoantibody, binding to the inventive polypeptide, comprising the steps a) contacting a sample comprising the antibody with the inventive polypeptide such that a complex is formed, b) isolating the complex formed in step a), c) dissociating the complex isolated in step b), and d) separating the antibody from the inventive polypeptide. A sample from a patient suffering from the novel neurological disorder identified by the inventors may be used as the source of antibody. Suitable methods are described in the state of the art, for example in the Handbooks "Affinity chromatography", "Strategies for Protein Purification" and "Antibody Purification" (2009/2010), published by GE Healthcare Life Sciences, and in Philips, Terry, M., Analytical techniques in immunochemistry, 1992, Marcel Dekker, Inc.

The invention provides a pharmaceutical composition comprising the inventive polypeptide, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject. In a preferred embodiment, the invention provides a vaccine comprising the inventive polypeptide, optionally comprising an auxiliary agent such as an adjuvant or a buffer, and the use of the inventive polypeptide for the preparation of a vaccine.

Within the scope of the present invention, a medical or diagnostic device comprising, preferably coated with the inventive (auto)antibody and/or the inventive polypeptide is provided. Preferably such a medical or diagnostic device comprises the inventive polypeptide in a form that allows contacting it with an aqueous solution, more preferably the liquid human sample, in a straightforward manner. In particular, the inventive polypeptide comprising may be immobilized on the surface of a carrier, preferably selected from the group comprising glass plates or slides, biochips, microtiter plates, beads, for example magnetic beads, apharesis devices, chromatography columns, membranes or the like. Exemplary medical devices include line blots, microtiterplates, glass slides for microscopy, beads and biochips. In addition to the inventive polypeptide, the medical or diagnostic device may comprise additional polypeptides, for example positive or negative controls or known other antigens binding to autoantibodies of diagnostic value, particularly those related other diseases associated with one or more identical or similar symptoms.

The inventive teachings provide a kit, preferably for diagnosing a disease. Such a kit may comprise instructions detailing how to use the kit and a means for contacting the inventive polypeptide with a bodily fluid sample from a subject, preferably a human subject, for example a line blot, wherein the inventive polypeptide is immobilized on the line blot. Furthermore, the kit may comprise a positive control, for example a batch of autoantibody or recombinant antibody known to bind to the inventive polypeptide and a negative control, for example a protein having no detectable affinity to the inventive polypeptide such as bovine serum albumin. Finally, such a kit may comprise a standard solution of the antibody or antigen for preparing a calibration curve.

In a preferred embodiment, the kit comprises a means for detecting an antibody, more preferably an autoantibody, binding to the inventive polypeptide, preferably by detecting a complex comprising the inventive polypeptide and an antibody binding to the inventive polypeptide. Such means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, preferably a secondary antibody specific for mammalian IgG class of antibodies. A multitude of methods and means for detecting such a complex have been described in the state of the art, for example in Philips, Terry, M., Analytical techniques in immunochemistry, 1992, Marcel Dekker, Inc.

The inventive polypeptide comprising RGS8 or a variant thereof may be produced or provided in the form of a cell comprising and/or expressing a nucleic acid encoding said polypeptide. If a nucleic acid comprising a sequence that encodes for the inventive polypeptide or variant thereof is used, such a nucleic acid may be an unmodified nucleic acid. In a preferred embodiment, the nucleic acid is a nucleic acid that, as such, does not occur in nature and comprises, compared to natural nucleic acid, at least one modification, for example an isotopic content or chemical modifications, for example a methylation, sequence modification, label or the like indicative of synthetic origin. In a preferred embodiment, the nucleic acid is a recombinant nucleic acid or part or a nucleic acid, and is, in a more preferred embodiment, part of a vector, in which it may be functionally linked with a promoter that allows for expression, preferably overexpression of the nucleic acid. The person skilled in the art is familiar with a variety of suitable vectors, of which are commercially available, for example from Origene. For example, a vector encoding for fusion constructs with a C-terminal GFP may be used. The cell may be a eukaryotic or prokaryotic cell, preferably of eukaryotic cell, such as a yeast cell, and is more preferably a mammalian, more preferably a human cell such as a HEK293 cell. Examples of a mammalian cell include a HEK293, CHO or COS-7 cell. The cell comprising the nucleic acid encoding for the inventive polypeptide may be a recombinant cell or an isolated cell wherein the term "isolated" means that the cell is enriched such that, compared to the environment of the wild type of said cell, fewer cells of other differentiation or species or in fact no such other cells are present.

The inventive teachings may not only be used for a diagnosis, but also for preventing or treating a disease, more specifically a method for preventing or treating a disease, comprising the steps a) reducing the concentration of autoantibodies binding to the inventive polypeptide in the subject's blood and/or b) administering one or more immunosuppressive pharmaceutical substances, preferably selected from the group comprising rituximab, prednisone, methylprednisolone, cyclophosphamide, mycophenolate-mofetil, intravenous immunoglobulin, tacrolimus, cyclosporine, methotrexate, azathioprine and/or the pharmaceutical composition.

The present invention provides a use of a means for the detection of an autoantibody to RGS8 or RGS8 or a variant thereof or of a nucleic acid encoding RGS8 or the variant or a vector or cell comprising said nucleic acid for the manufacture of kit for the diagnosis of a disease such as PNS or cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Cryosections were incubated with patient sera (1:32) in the first step, and with Alexa488-labelled goat anti-human IgG in the second step. Nuclei were counterstained by incubation with TO-PRO-3 iodide. A fine-granular staining of cerebellar molecular layer and Purkinje cells was obtained with the strongest reaction on the Purkinje cells.

Figure 2:
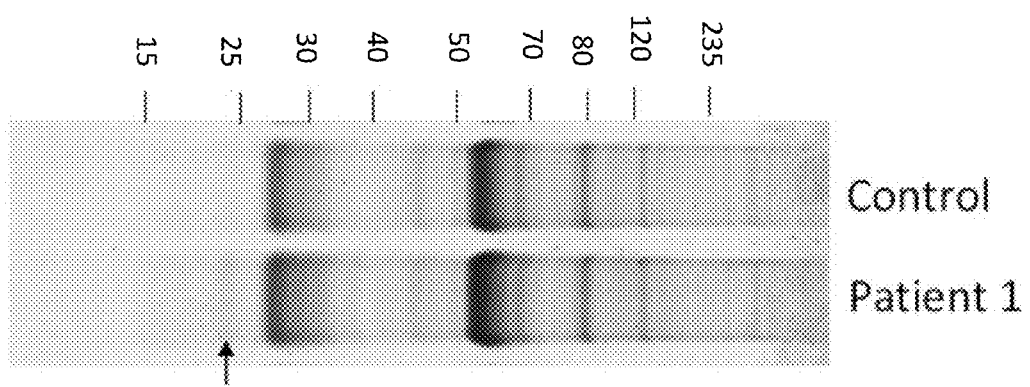

FIG. 2. Immunoprecipitation and antigen identification.

Lysates of rat cerebellum were incubated with patient or control sera (1:16.7). Immunocomplexes were isolated with protein-G-coated magnetic beads, eluted by SDS and subjected to SDS-PAGE analysis followed by staining with colloidal coomassie. Arrow indicates the position of the immunoprecipitated antigen at about 25 kDa.

Figure 3A:
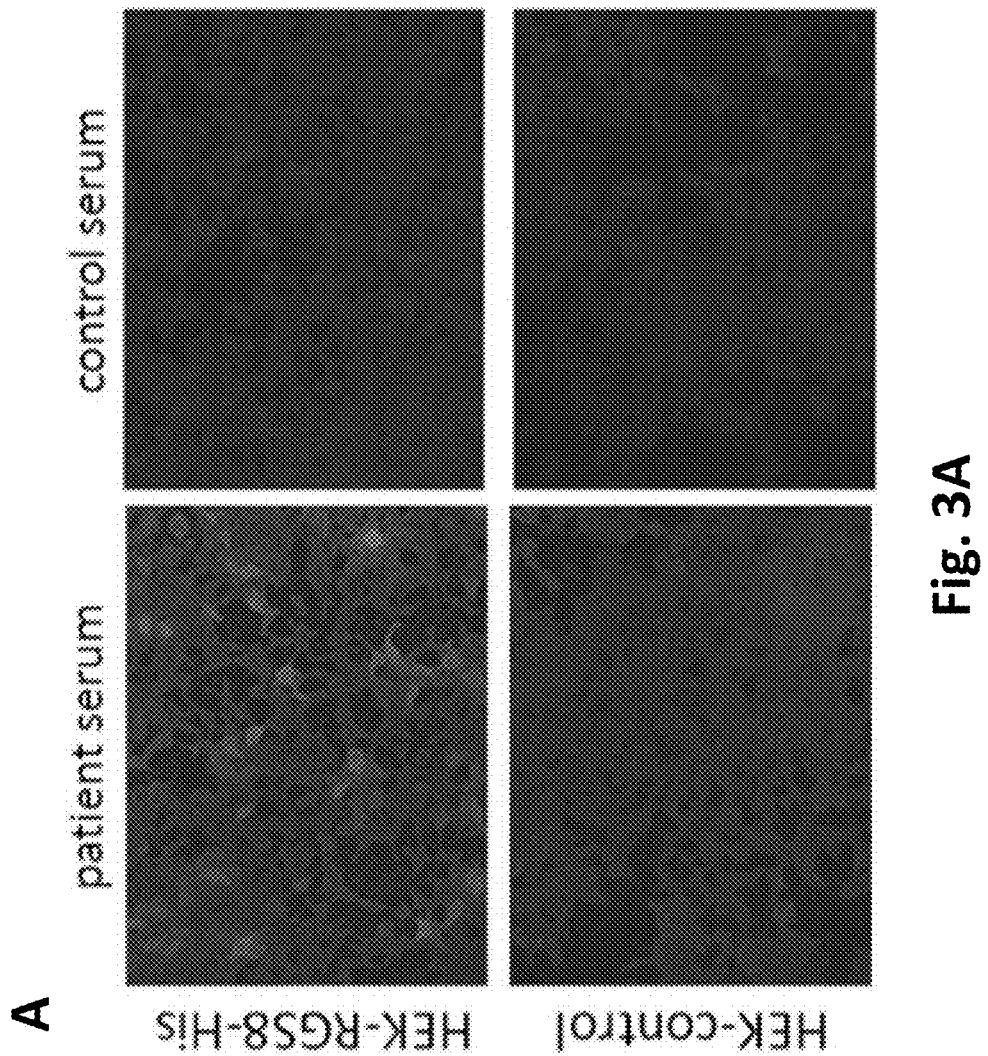
Figure 3B:
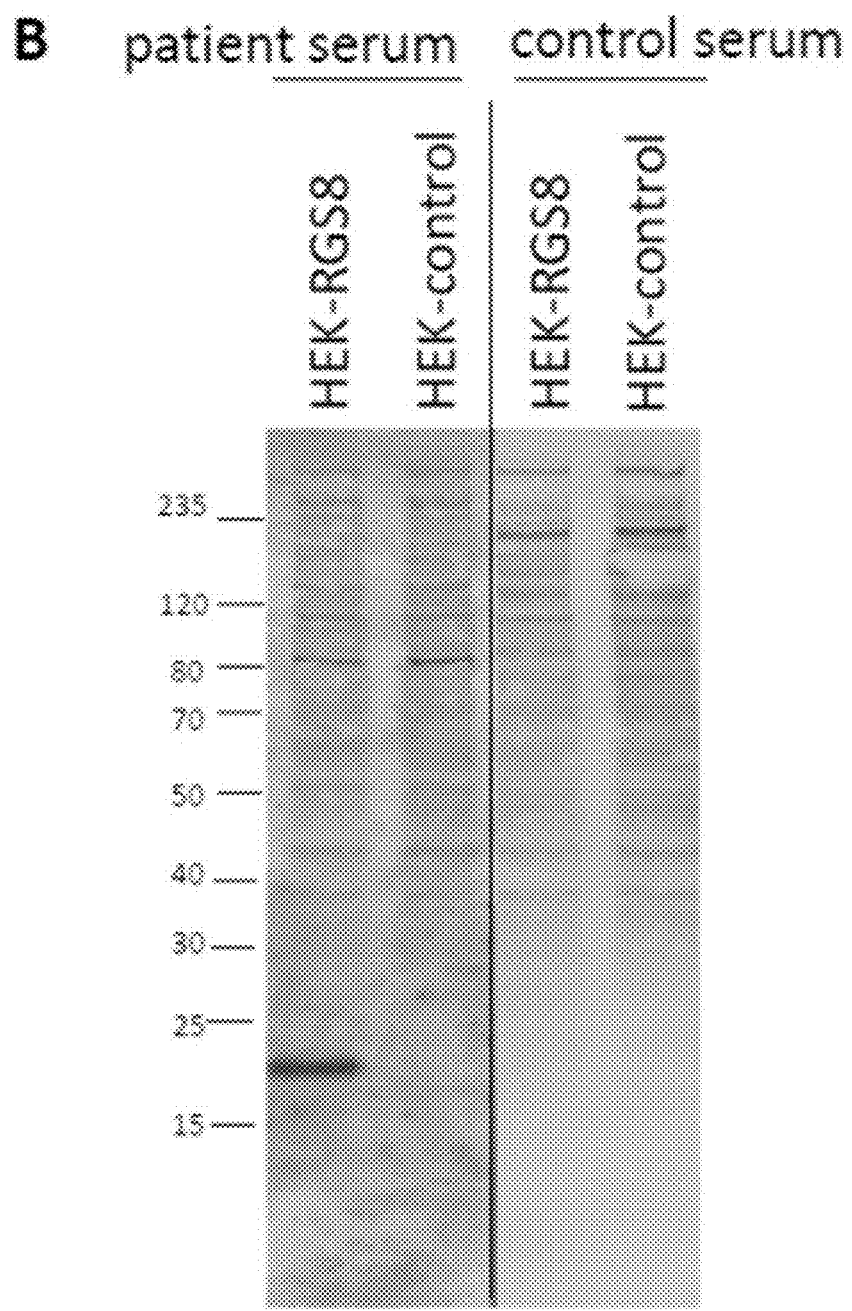
Figure 3C:
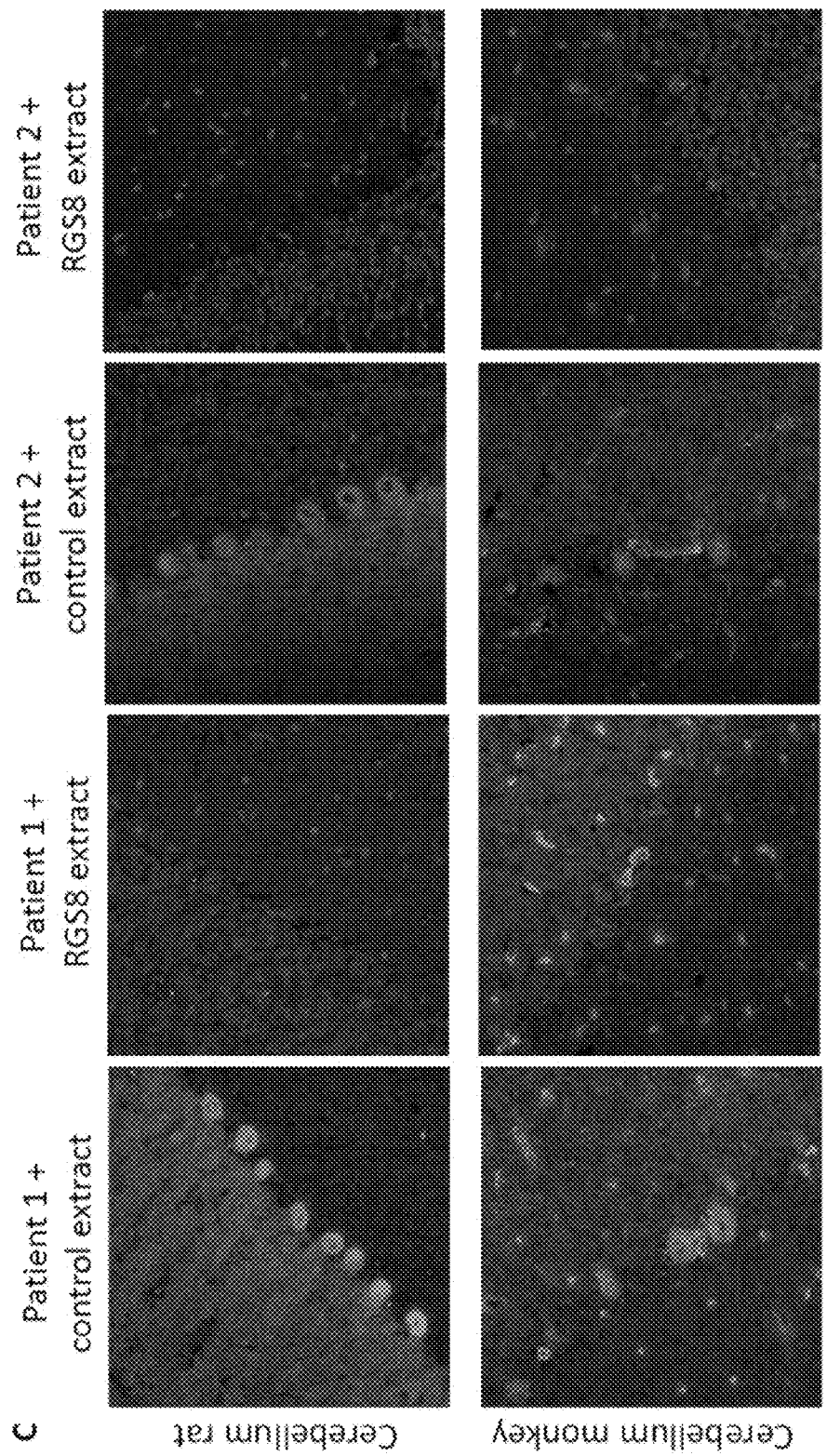

FIGS. 3A-3C. Verification of RGS8 as the novel autoantigen by indirect immunofluorescence and Western blot with the recombinant antigen.

FIG. 3A: Indirect immunofluorescence using acetone-fixed RGS8-His or mock-transfected HEK293 cells incubated with 1:10 diluted serum of patient 1 or a healthy control. FIG. 3B: Western blot with lysates of RGS8 or mock-transfected HEK293 cells incubated with 1:200 diluted serum of patient 2 or a healthy control. FIG. 3C: Neutralization of immunofluorescence reaction on neuronal tissues. Patient sera were pre-incubated with extracts of HEK293 cells transfected with RGS8 or with empty vector as control. The extract containing RGS8 abolished the immune reaction. Nuclei were counterstained by incubation with TO-PRO-3 iodide.

A number of sequences are disclosed in this application, more specifically SEQ ID NO:1 (RGS8 fused to C-terminal His tag) and SEQ ID NO:2 (RGS8 as expressed in the examples), SEQ ID NO:3 RGS8. SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15 represent antigenic sequences identified by mass spectrometry.

EXAMPLES

Summary
Methods:
Two patients (patient 1: 53 years, patient 2: 73 years) underwent neurological, neuroimaging and laboratory investigation. Sera and cerebrospinal fluids (CSF) were subjected to comprehensive autoantibody screening by indirect immunofluorescence assay (IFA) and immunoblot. Immunoprecipitation with lysates of cerebellum followed by mass spectrometry (MS) was used to identify the autoantigen, which was verified by recombinant expression in HEK293 cells and use in several immunoassays.

Results:

Both patients presented with cerebellar syndrome accompanied by a B-cell lymphoma of the stomach (patient 1) or a Hodgkin's lymphoma (patient 2). IFA screening revealed strong IgG reactivity in sera (patient 1/2: 1:320) and CSF (patient 1: 1:100) with cerebellar Purkinje cells and molecular layer, but not with a panel of 30 recombinantly expressed established neural auto-antigens. Regulator of G-protein signaling 8 (RGS8) was subsequently identified as the target antigen. The patient sera showed a specific reaction with recombinant expressed human RGS8 in IFA and immunoblot, whereas no such reactivity was detectable in 42 disease controls or in 48 healthy controls. In a neutralization experiment, recombinant RGS8 was able to neutralize the autoantibodies' tissue reaction.

These results show that the emergence and detection of an autoantibody is specifically linked to the emergence of PNS, more specifically cerebellar syndrome, and cancer such as lymphoma and, consequently, diagnostically useful.

Patients

Control collectives included 48 healthy donors, 42 patients with neurological symptoms and defined anti-neural autoantibodies (5× anti-NMDAR, 5× anti-Hu, 2× anti-Hu/anti-Ri, 6× anti-Yo, 2× anti-Yo/anti-Ri, 3× anti-Ri, 5× anti-AQP4, 5× anti-LGI1, 3× anti-CASPR2, 1× anti-mGluR5, 5× anti-SOX1).

Indirect Immunofluorescence Assay (IFA)

IFA was conducted using slides with a biochip array of brain tissue cryosections (hippocampus of rat, cerebellum of rat and monkey) combined with recombinant HEK293 cells separately expressing 30 different brain antigens Hu, Yo, Ri, CV2, PNMA2, ITPR1, Homer 3, CARP VIII, ARHGAP26, ZIC4, DNER/Tr, GAD65, GAD67, amphiphysin, recoverin, GABA$_B$ receptor, glycine receptor, DPPX, IgLON5, glutamate receptors (types NMDA, AMPA, mGluR1, mGluR5, GLURD2), LGI1, CASPR2, AQP4 (M1 and M23), MOG, ATP1A3, NCDN (EUROIMMUN, FA 111a-1003-51, FA 1112-1003-50, FA-1128-1003-50, FA112d-1003-1, FA 112m-1003-50, FA 1151-1003-50, Miske R, Hahn S, Rosenkranz T, Müller M, Dettmann I M, Mindorf S, Denno Y, Brakopp S, Scharf M, Teegen B, Probst C, Melzer N, Meinck H M, Terborg C, Stöcker W, Komorowski L., 2016, Autoantibodies against glutamate receptor δ2 after allogenic stem cell transplantation. Neurol Neuroimmunol Neuroinflamm., 3(4):e255; Scharf M, Miske R, Heidenreich F, Giess R, Landwehr P, Blöcker I M, Begemann N, Denno Y, Tiede S, Dahnrich C, Schlumberger W, Unger M, Teegen B, Stöcker W, Probst C, Komorowski L, 2015, Neuronal Na+/K+ ATPase is an autoantibody target in paraneoplastic neurologic syndrome, Neurology; 84(16):1673-9; Miske R, Gross C C, Scharf M, Golombeck K S, Hartwig M, Bhatia U, Schulte-Mecklenbeck A, Bönte K, Strippel C, Schöls L, Synofzik M, Lohmann H, Dettmann I M, Deppe M, Mindorf S, Warnecke T, Denno Y, Teegen B, Probst C, Brakopp S, Wandinger K P, Wiendl H, Stöcker W, Meuth S G, Komorowski L, Melzer N, 2016, Neurochondrin is a neuronal target antigen in autoimmune cerebellar degeneration, Neurol Neuroimmunol Neuroinflamm.; 4(1):e307)). Each biochip mosaic was incubated with 70 μL of PBS-diluted sample at room temperature for 30 min, washed with PBS-Tween and immersed in PBS-Tween for 5 min. In the second step, either Alexa488-labelled goat anti-human IgG (Jackson Research, Suffolk, United Kingdom), or fluorescein isothiocyanate (FITC)-labelled goat anti-human IgG (EUROIMMUN Medizinische Labordiagnostika AG, Lübeck) were applied and incubated at room temperature for 30 min. Slides were washed again with a flush of PBS-Tween and then immersed in PBS-Tween for 5 min. Slides were embedded in PBS-buffered, DABCO containing glycerol (approximately 20 μL per field) and examined by fluorescence microscopy. Positive and negative controls were included. Samples were classified as positive or negative based on fluorescence intensity of the transfected cells in direct comparison with non-transfected cells and control samples. Endpoint titers refer to the last dilution showing visible fluorescence.

In competitive inhibition experiments, recombinant RGS8 was mixed with diluted serum sample 1 h prior to the IFA. Results were evaluated by two independent observers using a laser scanning microscope (LSM700, Zeiss, Jena, Germany). Reagents were obtained from Merck, Darmstadt, Germany or Sigma-Aldrich, Heidelberg, Germany if not specified otherwise.

Immunoblot

Lysate of HEK-RGS8 cells expressing SEQ ID NO:2 in 0.1% Triton-X-100, 1 mM EDTA buffer, 150 mM NaCl, 100 mM Tris pH 7.4 was incubated with NuPage LDS sample buffer (ThermoFisher Scientific, Schwerte, Germany) containing 25 mmol/L dithiothreitol at 70° C. for 10 minutes, followed by SDS-PAGE (NuPAGE, ThermoFisher Scientific, Schwerte, Germany). Separated proteins were electrotransferred onto a nitrocellulose membrane by tank blotting with transfer buffer (ThermoFisher Scientific) according to the manufacturer's instructions. The membranes were blocked with Universal Blot Buffer plus (EUROIMMUN Medizinische Labordiagnostika AG, Lübeck) for 15 min and incubated with the patient or control sera (dilution 1:200) in Universal Blot Buffer plus for 3 hours, followed by 3 washing steps with Universal Blot Buffer (EUROIMMUN Medizinische Labordiagnostika AG, Lübeck), a second incubation for 30 min with anti-human-IgG-AP (EUROIMMUN Medizinische Labordiagnostika AG, Lübeck), 3 washing steps, and staining with NBT/BCIP substrate (EUROIMMUN Medizinische Labordiagnostika AG, Lübeck). Reagents were obtained from Merck, Darmstadt, Germany or Sigma-Aldrich, Heidelberg, Germany if not specified otherwise.

For the detection of anti-SOX1 reactivity a line blot was performed (EUROIMMUN, DL 1111-1601-6 G) according to manufacturer's instructions.

Identification of the Antigen

Cerebellum from rat was dissected and shock-frozen in liquid nitrogen. The tissues were homogenised in solubilization buffer (100 mmol/L tris-HCl pH 7.4, 150 mmol/L sodium chloride, 2.5 mmol/L ethylenediamine tetraacetic acid, 0.5% (w/v) sodium deoxycholate, 1% (w/v) Triton X-100) containing protease inhibitors (Complete mini, Roche Diagnostics, Penzberg, Germany) with a Miccra D-8 (Roth, Karlsruhe, Germany) and a hand homogenizer (Sartorius, Gottingen, Germany) at 4° C. The tissue lysates was centrifuged at 21,000×g at 4° C. for 15 min and clear supernatants were incubated with patient's serum (diluted 1:16.7) at 4° C. overnight. The samples were then incubated with Protein G Dynabeads (ThermoFisher Scientific, Dreieich, Germany) at 4° C. for 3 h to capture immunocomplexes.

Beads were washed 3 times with PBS, and eluted with NuPage LDS sample buffer (ThermoFisher Scientific, Schwerte, Germany) containing 25 mmol/L dithiothreitol at 70° C. for 10 min. Carbamidomethylation with 59 mM iodoacetamide (Bio-Rad, Hamburg, Germany) was performed prior to SDS-PAGE (NuPAGE, ThermoFisher Scientific, Schwerte, Germany). Separated proteins were visualized with Coomassie Brillant Blue (G-250) (Merck), and identified by mass spectrometric analysis. Peptides consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15 were identified.

Mass Spectrometry

Visible protein bands were excised from Coomassie Brilliant Blue G-250 stained gels. After destaining and tryptic digestion peptides were extracted and spotted with α-cyano-4-hydroxycinnamic acid onto a MTP AnchorChip™ 384 TF target.

MALDI-TOF/TOF measurements were performed with an Autoflex III smartbeam TOF/TOF200 System using flexControl 3.4 software. MS spectra for peptide mass fingerprinting (PMF) were recorded in positive ion reflector mode with 4,000-10,000 shots and in a mass range from 600 Da to 4,000 Da. Spectra were calibrated externally with the commercially available Peptide Calibration Standard II, processed with flexAnalysis 3.4 and peak lists were analyzed with BioTools 3.2.

The Mascot search engine Mascot Server 2.3 (Matrix Science, London, UK) was used for protein identification by searching against the NCBI or SwissProt database limited to Mammalia. Search parameters were as follows: Mass tolerance was set to 80 ppm, one missed cleavage site was accepted, and carbamidomethylation of cysteine residues as well as oxidation of methionine residues were set as fixed and variable modifications, respectively. To evaluate the protein hits, a significance threshold of $p<0.05$ was chosen.

For further confirmation of the PMF hits two to five peptides of each identified protein were selected for MS/MS measurements using the WARP feedback mechanism of BioTools. Parent and fragment masses were recorded with 400 and 1000 shots, respectively. Spectra were processed and analyzed as described above with a fragment mass tolerance of 0.7 Da.

Recombinant Expression of RGS8 in HEK293

The coding DNA for human RGS8 (UNIPROT acc. #P57771 was obtained by PCR on commercially available cDNA (IRATp970H06133D, Source BioScience, Nottingham, UK) and primers ATACGTCTCACATGGCGGCCT-TACTGATGCCACGC (SEQ ID NO: 19) [sense RGS8] and ATACGTCTCCTCGAGACTGAGCCTCCTCTGGCT-TTGGGAC (SEQ ID NO: 20) [asense RGS8] or ATACGTCTCCTCGAGCTAACTGAGCCTCCTCTG-GCTTTGG (SEQ ID NO: 21) [asense RGS8-Stop]. The amplification products were digested with Esp3I and DpnI and ligated with pTriEx-1 (Merck, Darmstadt, Germany). RGS8-His or RGS8 (dHis) was expressed in the human cell line HEK293 after ExGen500-mediated transfection (ThermoFisher Scientific) according to the manufacturer's instructions. In order to prepare substrates for IFA, HEK293 were seeded on sterile cover glasses, transfected, and allowed to express RGS8-His or RGS8 (dHis) for 48 hours. Cover glasses were washed with PBS, fixed with acetone for 10 minutes at room temperature, air-dried, cut into millimeter-sized biochips and used as substrates in IFA as described.

Alternatively, cells were transfected in standard T-flasks and the cells were harvested after 5 days. The cell sediment was extracted with solubilization buffer. The extracts were stored in aliquots at −80° C. until further use.

Characterization of the Patients' Auto-Antibodies

Figure 1:
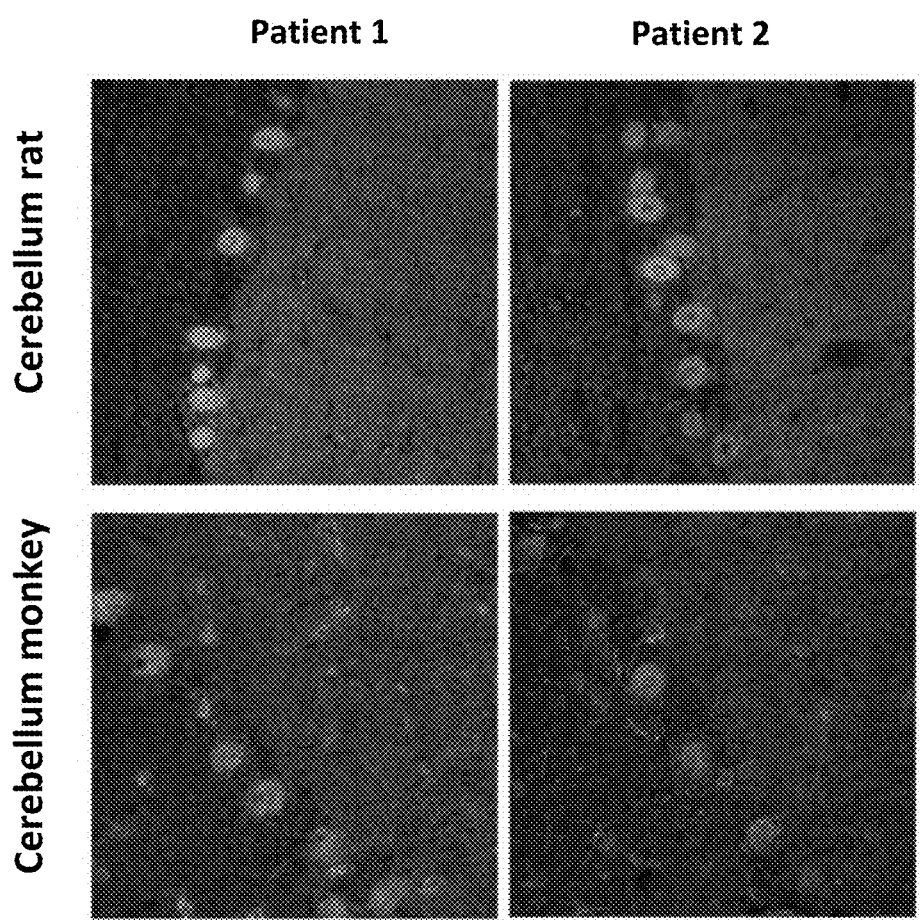
FIG. 1. Immunofluorescence staining of cerebellum.

Indirect immunofluorescence assays (IFA) of patients' sera and CSF using permeabilized cryosections of cerebellum showed a fine-granular IgG staining of the Purkinje cells and the molecular layer (FIG. 1). The patients had serum titers of 1:320 (patient 1 and 2) and CSF titers of 1:100 (patient 1) as determined with rat cerebellum. Further monospecific analyses were conducted with recombinant HEK293 cells expressing 30 neural autoantigens: Hu, Yo, Ri, CV2, PNMA2, SOX1, ITPR1, Homer 3, CARP VIII, ARHGAP26, ZIC4, DNER/Tr, GAD65, GAD67, amphiphysin, recoverin, GABAB receptor, glycine receptor, DPPX, IgLON5, glutamate receptors (types NMDA, AMPA, mGluR1, mGluR5, GLURD2), LGI1, CASPR2, AQP4 (M1 and M23), MOG, ATP1A3 and NCDN or a line blot spotted with SOX1. In patient 2, but not patient 1, weak anti-Sox1 reactivity was detected. No other specific reactivity was observed.

Identification of RGS8 as the Target Neuronal Auto-Antigen

Immunoprecipitates from homogenized rat cerebellum obtained with the patients' sera, presented a protein of approximately 25 kDa in SDS-PAGE which was absent if the homogenates were incubated with normal control sera (FIG. 2). Using MALDI-TOF, the 25 kDa protein fraction was identified as regulator of G-protein signaling 8 (RGS8) from *Rattus norvegicus* (UNIPROT acc. #P49804).

As a proof for correct antigen identification, the patients' samples were tested by IFA using transfected HEK293 cells which expressed RGS8-His (SEQ ID NO:1) (FIG. 3A). Patients' sera and CSFs reacted with the RGS8-His-expressing cells. All samples also reacted with recombinant RGS8 in immunoblot using HEK293-RGS8 lysate (FIG. 3B). In contrast, mock-transfected cell did not demonstrate any specific antibody binding.

The reaction of the patients' auto-antibodies on tissue could be abolished by pre-incubation with HEK293 lysate containing RGS8 (SEQ ID NO:2) (FIG. 3C). Antibody binding was unaffected when a comparable fraction from mock-transfected HEK293 cells was used.

Specificity of Anti-RGS8 Auto-Antibodies for Autoimmune Cerebellar Degeneration

Sera from 42 patients with various neural auto-antibody-associated neurological syndromes in part also involving cerebellum and brainstem (5× anti-NMDAR, 5× anti-Hu, 2× anti-Hu/anti-Ri, 6× anti-Yo, 2× anti-Yo/anti-Ri, 3× anti-Ri, 5× anti-AQP4, 5× anti-LGI1, 3× anti-CASPR2, 1× anti-mGluR5, 5× anti-SOX1), and 48 healthy controls were analyzed by IFA and with HEK293-RGS8-His in parallel to the samples of the patients. None of the control sera produced a similar immunofluorescence pattern as the patients' sera on rat brain tissue, and all were all negative when tested on HEK293 cells expressing RGS8. Hence, we consider IgG antibodies against RGS8 specific for patients with PCD.

The invention claimed is:

1. A method of determining the presence or absence of an autoantibody to Regulator of G-protein signaling 8 (RGS8) in a subject, comprising:
   contacting a sample isolated from a subject having paraneoplastic cerebellar degeneration (PCD) with a polypeptide comprising RGS8, wherein the polypeptide comprising RGS8 binds specifically to autoantibodies binding to RGS8, and
   determining the presence or absence of an autoantibody to RGS8 in a complex with the polypeptide.

2. The method according to claim 1, wherein the subject has PCD that is associated with one or more symptoms selected from the group consisting of dysarthria, dysphagia, nystagmus, oscillopsia, vertigo, nausea, ataxia dizziness, seizures, epilepsy and tremor.

3. The method according to claim 1, wherein the PCD is associated with a cancer selected from the group consisting of Hodgkin lymphoma, non-Hodgkin lymphoma, small cell lung and breast cancer.

4. The method according to claim 1, wherein the sample is a bodily fluid comprising autoantibodies, or the sample is a tumor biopsy.

5. The method according to claim 1, wherein the sample is a bodily fluid selected from the group consisting of whole blood, serum, cerebrospinal fluid, and saliva.

* * * * *

UNITED STATES PATENT AND TRADEMARK OFFICE
CERTIFICATE OF CORRECTION

PATENT NO. : 10,466,239 B2  
APPLICATION NO. : 15/954019  
DATED : November 5, 2019  
INVENTOR(S) : Winfried Stoecker et al.

Page 1 of 1

It is certified that error appears in the above-identified patent and that said Letters Patent is hereby corrected as shown below:

On the Title Page

"(73) Assignee: "EUROIMMUN MEDIZINISHE LABORDIAGNOSTIKA AG, Lübeck, (DE)"  
Should read:  
--(73) Assignee: EUROIMMUN MEDIZINISCHE LABORDIAGNOSTIKA AG, Lübeck, (DE)--

Signed and Sealed this  
Ninth Day of June, 2020

Andrei Iancu  
*Director of the United States Patent and Trademark Office*

SEQUENCE LISTING

<160> NUMBER OF SEQ ID NOS: 21

<210> SEQ ID NO 1
<211> LENGTH: 190
<212> TYPE: PRT
<213> ORGANISM: Artificial Sequence
<220> FEATURE:
<223> OTHER INFORMATION: RGS8[human]-His

<400> SEQUENCE: 1

Met Ala Ala Leu Leu Met Pro Arg Arg Asn Lys Gly Met Arg Thr Arg
1               5                   10                  15

Leu Gly Cys Leu Ser His Lys Ser Asp Ser Cys Ser Asp Phe Thr Ala
            20                  25                  30

Ile Leu Pro Asp Lys Pro Asn Arg Ala Leu Lys Arg Leu Ser Thr Glu
        35                  40                  45

Glu Ala Thr Arg Trp Ala Asp Ser Phe Asp Val Leu Leu Ser His Lys
50                  55                  60

Tyr Gly Val Ala Ala Phe Arg Ala Phe Leu Lys Thr Glu Phe Ser Glu
65                  70                  75                  80

Glu Asn Leu Glu Phe Trp Leu Ala Cys Glu Phe Lys Lys Thr Arg
            85                  90                  95

Ser Thr Ala Lys Leu Val Ser Lys Ala His Arg Ile Phe Glu Glu Phe
            100                 105                 110

Val Asp Val Gln Ala Pro Arg Glu Val Asn Ile Asp Phe Gln Thr Arg
            115                 120                 125

Glu Ala Thr Arg Lys Asn Leu Gln Glu Pro Ser Leu Thr Cys Phe Asp
        130                 135                 140

Gln Ala Gln Gly Lys Val His Ser Leu Met Glu Lys Asp Ser Tyr Pro
145                 150                 155                 160

Arg Phe Leu Arg Ser Lys Met Tyr Leu Asp Leu Leu Ser Gln Ser Gln
            165                 170                 175

Arg Arg Leu Ser Leu Glu His His His His His His
            180                 185                 190

<210> SEQ ID NO 2
<211> LENGTH: 180
<212> TYPE: PRT
<213> ORGANISM: Homo sapiens
<220> FEATURE:
<223> OTHER INFORMATION: RGS8[human]

<400> SEQUENCE: 2

Met Ala Ala Leu Leu Met Pro Arg Arg Asn Lys Gly Met Arg Thr Arg
1               5                   10                  15

Leu Gly Cys Leu Ser His Lys Ser Asp Ser Cys Ser Asp Phe Thr Ala
            20                  25                  30

Ile Leu Pro Asp Lys Pro Asn Arg Ala Leu Lys Arg Leu Ser Thr Glu
        35                  40                  45

Glu Ala Thr Arg Trp Ala Asp Ser Phe Asp Val Leu Leu Ser His Lys
50                  55                  60

Tyr Gly Val Ala Ala Phe Arg Ala Phe Leu Lys Thr Glu Phe Ser Glu
65                  70                  75                  80

Glu Asn Leu Glu Phe Trp Leu Ala Cys Glu Phe Lys Lys Thr Arg
            85                  90                  95

Ser Thr Ala Lys Leu Val Ser Lys Ala His Arg Ile Phe Glu Glu Phe
            100                 105                 110

Val Asp Val Gln Ala Pro Arg Glu Val Asn Ile Asp Phe Gln Thr Arg
            115                 120                 125

Glu Ala Thr Arg Lys Asn Leu Gln Glu Pro Ser Leu Thr Cys Phe Asp
        130                 135                 140

Gln Ala Gln Gly Lys Val His Ser Leu Met Glu Lys Asp Ser Tyr Pro
145                 150                 155                 160

Arg Phe Leu Arg Ser Lys Met Tyr Leu Asp Leu Leu Ser Gln Ser Gln
                165                 170                 175

Arg Arg Leu Ser
            180

<210> SEQ ID NO 3
<211> LENGTH: 180
<212> TYPE: PRT
<213> ORGANISM: Rattus norvegicus
<220> FEATURE:
<223> OTHER INFORMATION: RGS8[rat]

<400> SEQUENCE: 3

Met Ala Ala Leu Leu Met Pro Arg Arg Asn Lys Gly Met Arg Thr Arg
1               5                   10                  15

Leu Gly Cys Leu Ser His Lys Ser Asp Ser Cys Ser Asp Phe Thr Ala
            20                  25                  30

Ile Leu Pro Asp Lys Pro Asn Arg Ala Leu Lys Arg Leu Ser Thr Glu
        35                  40                  45

Glu Ala Thr Arg Trp Ala Asp Ser Phe Asp Val Leu Leu Ser His Lys
    50                  55                  60

Tyr Gly Val Ala Ala Phe Arg Ala Phe Leu Lys Thr Glu Phe Ser Glu
65                  70                  75                  80

Glu Asn Leu Glu Phe Trp Leu Ala Cys Glu Glu Phe Lys Lys Thr Arg
                85                  90                  95

Ser Thr Ala Lys Leu Val Thr Lys Ala His Arg Ile Phe Glu Glu Phe
            100                 105                 110

Val Asp Val Gln Ala Pro Arg Glu Val Asn Ile Asp Phe Gln Thr Arg
        115                 120                 125

Glu Ala Thr Arg Lys Asn Met Gln Glu Pro Ser Leu Thr Cys Phe Asp
    130                 135                 140

Gln Ala Gln Gly Lys Val His Ser Leu Met Glu Lys Asp Ser Tyr Pro
145                 150                 155                 160

Arg Phe Leu Arg Ser Lys Met Tyr Leu Asp Leu Leu Ser Gln Ser Gln
                165                 170                 175

Arg Arg Leu Ser
            180

<210> SEQ ID NO 4
<211> LENGTH: 12
<212> TYPE: PRT
<213> ORGANISM: Artificial Sequence
<220> FEATURE:
<223> OTHER INFORMATION: synthetic sequence - aa 53 to aa 64 of SEQ ID
      NO 3

<400> SEQUENCE: 4

Trp Ala Asp Ser Phe Asp Val Leu Leu Ser His Lys
1               5                   10

<210> SEQ ID NO 5
<211> LENGTH: 19
<212> TYPE: PRT

```
<213> ORGANISM: Artificial Sequence
<220> FEATURE:
<223> OTHER INFORMATION: synthetic sequence - aa 53 to aa 71 of SEQ ID
      NO 3

<400> SEQUENCE: 5

Trp Ala Asp Ser Phe Asp Val Leu Leu Ser His Lys Tyr Gly Val Ala
1               5                   10                  15

Ala Phe Arg

<210> SEQ ID NO 6
<211> LENGTH: 7
<212> TYPE: PRT
<213> ORGANISM: Artificial Sequence
<220> FEATURE:
<223> OTHER INFORMATION: synthetic sequence -aa 65 to aa 71 of SEQ ID
      NO 3

<400> SEQUENCE: 6

Tyr Gly Val Ala Ala Phe Arg
1               5

<210> SEQ ID NO 7
<211> LENGTH: 19
<212> TYPE: PRT
<213> ORGANISM: Artificial Sequence
<220> FEATURE:
<223> OTHER INFORMATION: synthetic sequence -aa 76 to aa 94 of SEQ ID
      NO 3

<400> SEQUENCE: 7

Thr Glu Phe Ser Glu Glu Asn Leu Glu Phe Trp Leu Ala Cys Glu Glu
1               5                   10                  15

Phe Lys Lys

<210> SEQ ID NO 8
<211> LENGTH: 15
<212> TYPE: PRT
<213> ORGANISM: Artificial Sequence
<220> FEATURE:
<223> OTHER INFORMATION: synthetic sequence -aa 105 to aa 119 of SEQ ID
      NO 3

<400> SEQUENCE: 8

Ala His Arg Ile Phe Glu Glu Phe Val Asp Val Gln Ala Pro Arg
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: synthetic sequence -aa 108 to aa 119 of SEQ ID
      NO 3

<400> SEQUENCE: 9

Ile Phe Glu Glu Phe Val Asp Val Gln Ala Pro Arg
1               5                   10

<210> SEQ ID NO 10
<211> LENGTH: 21
<212> TYPE: PRT
<213> ORGANISM: Artificial Sequence
<220> FEATURE:
<223> OTHER INFORMATION: synthetic sequence -aa 108 to aa 128 of SEQ ID
      NO 3
```

```
<400> SEQUENCE: 10

Ile Phe Glu Glu Phe Val Asp Val Gln Ala Pro Arg Glu Val Asn Ile
1               5                   10                  15

Asp Phe Gln Thr Arg
            20

<210> SEQ ID NO 11
<211> LENGTH: 9
<212> TYPE: PRT
<213> ORGANISM: Artificial Sequence
<220> FEATURE:
<223> OTHER INFORMATION: synthetic sequence -aa 120 to aa 128 of SEQ ID
      NO 3

<400> SEQUENCE: 11

Glu Val Asn Ile Asp Phe Gln Thr Arg
1               5

<210> SEQ ID NO 12
<211> LENGTH: 17
<212> TYPE: PRT
<213> ORGANISM: Artificial Sequence
<220> FEATURE:
<223> OTHER INFORMATION: synthetic sequence -aa 134 to aa 149 of SEQ ID
      NO 3

<400> SEQUENCE: 12

Asn Met Gln Glu Pro Ser Leu Thr Cys Phe Asp Gln Ala Gln Gly Lys
1               5                   10                  15

Val

<210> SEQ ID NO 13
<211> LENGTH: 12
<212> TYPE: PRT
<213> ORGANISM: Artificial Sequence
<220> FEATURE:
<223> OTHER INFORMATION: synthetic sequence -aa 150 to aa 161 of SEQ ID
      NO 3

<400> SEQUENCE: 13

Val His Ser Leu Met Glu Lys Asp Ser Tyr Pro Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: synthetic sequence -aa 165 to aa 177 of SEQ ID
      NO 3

<400> SEQUENCE: 14

Ser Lys Met Tyr Leu Asp Leu Leu Ser Gln Ser Gln Arg
1               5                   10

<210> SEQ ID NO 15
<211> LENGTH: 11
<212> TYPE: PRT
<213> ORGANISM: Artificial Sequence
<220> FEATURE:
<223> OTHER INFORMATION: synthetic sequence -aa 167 to aa 177 of SEQ ID
      NO 3

<400> SEQUENCE: 15

Met Tyr Leu Asp Leu Leu Ser Gln Ser Gln Arg
1               5                   10
```

<210> SEQ ID NO 16
<211> LENGTH: 198
<212> TYPE: PRT
<213> ORGANISM: Homo sapiens
<220> FEATURE:
<223> OTHER INFORMATION: RGS8[human] P57771-isoform 2

<400> SEQUENCE: 16

Met Trp Asn Thr Leu Thr Arg Ser Leu Ser Asp His Pro Val Gly Lys
1               5                   10                  15

Asp Pro Gln Ala Met Arg Thr Gly Gln Arg Gln Asn Lys Gly Met Arg
            20                  25                  30

Thr Arg Leu Gly Cys Leu Ser His Lys Ser Asp Ser Cys Ser Asp Phe
        35                  40                  45

Thr Ala Ile Leu Pro Asp Lys Pro Asn Arg Ala Leu Lys Arg Leu Ser
    50                  55                  60

Thr Glu Glu Ala Thr Arg Trp Ala Asp Ser Phe Asp Val Leu Leu Ser
65                  70                  75                  80

His Lys Tyr Gly Val Ala Ala Phe Arg Ala Phe Leu Lys Thr Glu Phe
                85                  90                  95

Ser Glu Glu Asn Leu Glu Phe Trp Leu Ala Cys Glu Glu Phe Lys Lys
            100                 105                 110

Thr Arg Ser Thr Ala Lys Leu Val Ser Lys Ala His Arg Ile Phe Glu
        115                 120                 125

Glu Phe Val Asp Val Gln Ala Pro Arg Glu Val Asn Ile Asp Phe Gln
    130                 135                 140

Thr Arg Glu Ala Thr Arg Lys Asn Leu Gln Glu Pro Ser Leu Thr Cys
145                 150                 155                 160

Phe Asp Gln Ala Gln Gly Lys Val His Ser Leu Met Glu Lys Asp Ser
                165                 170                 175

Tyr Pro Arg Phe Leu Arg Ser Lys Met Tyr Leu Asp Leu Leu Ser Gln
            180                 185                 190

Ser Gln Arg Arg Leu Ser
        195

<210> SEQ ID NO 17
<211> LENGTH: 543
<212> TYPE: DNA
<213> ORGANISM: Artificial Sequence
<220> FEATURE:
<223> OTHER INFORMATION: cDNA of RGS8[human] isoform 1

<400> SEQUENCE: 17
atggcggcct tactgatgcc acgcaggaac aaagggatga ggactcgact gggatgcctg     60
tctcacaagt cagactcgtg tagtgatttc acagctattc ttccagacaa acccaaccgc    120
gctctcaaga gattatcgac agaagaagct acgaggtggg cagattcctt tgatgtgctt    180
ctctctcata gtatggggt ggctgcattc cgtgccttct tgaagacgga gttcagtgag    240
gagaacctgg aattctggtt ggcctgtgag gagttcaaga agaccaggtc aactgcaaaa    300
ctggtctcta aggcccatag gatctttgag gagtttgtgg atgtgcaggc tccacgggag    360
gtaaacattg acttccagac ccgagaagcc acgaggaaga acctgcagga gccatccctg    420
acttgctttg accaagccca aggaaaagta cacagcctca tggagaaaga ctcttacccc    480
aggttcctga ggtccaaaat gtacttagat ctgctgtccc aaagccagag gaggctcagt    540
tag                                                                  543

<210> SEQ ID NO 18
<211> LENGTH: 597
<212> TYPE: DNA
<213> ORGANISM: Artificial Sequence
<220> FEATURE:
<223> OTHER INFORMATION: cDNA of RGS8[human] isoform 2

<400> SEQUENCE: 18

```
atgtggaaca ccttaacccg aagcctctct gaccatccag ttggcaaaga ccctcaggcc      60
atgaggactg gccaaagaca gaacaaaggg atgaggactc gactgggatg cctgtctcac     120
aagtcagact cgtgtagtga tttcacagct attcttccag acaaacccaa ccgcgctctc     180
aagagattat cgacagaaga agctacgagg tgggcagatt cctttgatgt gcttctctct     240
cataagtatg gggtggctgc attccgtgcc ttcttgaaga cggagttcag tgaggagaac     300
ctggaattct ggttggcctg tgaggagttc aagaagacca ggtcaactgc aaaactggtc     360
tctaaggccc ataggatctt tgaggagttt gtggatgtgc aggctccacg ggaggtaaac     420
attgacttcc agacccgaga agccacgagg aagaacctgc aggagccatc cctgacttgc     480
tttgaccaag cccaaggaaa agtacacagc ctcatggaga aagactctta ccccaggttc     540
ctgaggtcca aaatgtactt agatctgctg tcccaaagcc agaggaggct cagttag        597
```

<210> SEQ ID NO 19
<211> LENGTH: 35
<212> TYPE: DNA
<213> ORGANISM: Artificial Sequence
<220> FEATURE:
<223> OTHER INFORMATION: Primer sense RGS8

<400> SEQUENCE: 19

```
atacgtctca catggcggcc ttactgatgc cacgc                                 35
```

<210> SEQ ID NO 20
<211> LENGTH: 40
<212> TYPE: DNA
<213> ORGANISM: Artificial Sequence
<220> FEATURE:
<223> OTHER INFORMATION: Primer asense RGS8

<400> SEQUENCE: 20

```
atacgtctcc tcgagactga gcctcctctg gctttgggac                            40
```

<210> SEQ ID NO 21
<211> LENGTH: 40
<212> TYPE: DNA
<213> ORGANISM: Artificial Sequence
<220> FEATURE:
<223> OTHER INFORMATION: Primer asense RGS8-Stop

<400> SEQUENCE: 21

```
atacgtctcc tcgagctaac tgagcctcct ctggctttgg                            40
```